(12) United States Patent  (10) Patent No.: US 8,532,784 B2
Sherman  (45) Date of Patent: Sep. 10, 2013

(54) DIRECT MEMORY ACCESS (DMA) CONTROLLED STIMULATION

(75) Inventor: Neil S. Sherman, San Bruno, CA (US)

(73) Assignee: Spinal Modulation, Inc., Menlo Park, CA (US)

( * ) Notice: Subject to any disclaimer, the term of this patent is extended or adjusted under 35 U.S.C. 154(b) by 157 days.

(21) Appl. No.: 13/023,470

(22) Filed: Feb. 8, 2011

(65) Prior Publication Data

US 2012/0158096 A1 Jun. 21, 2012

Related U.S. Application Data

(60) Provisional application No. 61/423,995, filed on Dec. 16, 2010.

(51) Int. Cl.
*A61N 1/37* (2006.01)

(52) U.S. Cl.
USPC ............................................................ 607/59

(58) Field of Classification Search
USPC ................................................................ 607/59
See application file for complete search history.

(56) References Cited

U.S. PATENT DOCUMENTS

| | | | |
|---|---|---|---|
| 4,407,288 A | 10/1983 | Langer et al. | |
| 5,297,242 A | 3/1994 | Miki | |
| 6,717,992 B2 | 4/2004 | Cowie et al. | |
| 7,296,170 B1 | 11/2007 | Richmond et al. | |
| 2007/0078498 A1 | 4/2007 | Rezai et al. | |
| 2008/0208284 A1 | 8/2008 | Rezai et al. | |
| 2009/0259278 A1 | 10/2009 | Torgerson et al. | |

OTHER PUBLICATIONS

International Search Report for PCT/US2011/063115, dated Mar. 21, 2012.
Texas Instruments, User's Guide SLAU208F, Jun. 2008 (Revised Dec. 2010), Chapter 9: DMA Controller, pp. 293-314.
Texas Instruments, User's Guide SLAU144F, Dec. 2010, Mixed Signal Products, Chapters 1, 5, 6, 8 and 12, 99 pages.

*Primary Examiner* — Joseph Dietrich
(74) *Attorney, Agent, or Firm* — Vierra Magen Marcus LLP

(57) ABSTRACT

An implantable stimulation system (e.g., an implantable neurostimulation system (INS)) comprises memory including a first table and a second table. The first table stores blocks of stimulation event data corresponding to stimulation events that are to be performed during a period of time (e.g., a 0.5 sec. or 1 sec. period of time). The second table stores blocks of next stimulation event time data corresponding to the period of time. The implantable stimulation system also includes a direct memory access (DMA) controller including a first DMA channel and a second DMA channel. The first DMA channel selectively transfers one of the blocks stimulation event data from the first table to one or more registers that are used to control stimulation events. The second DMA channel selectively transfers one of the blocks of next stimulation event time data from the second table to a timer that is used to control timing associated with the stimulation events. In this manner, the DMA controller is able to control stimulation.

28 Claims, 7 Drawing Sheets

DIRECT MEMORY ACCESS (DMA) CONTROLLED STIMULATION

PRIORITY CLAIM

The present application claims priority under 35 U.S.C. 119(e) to U.S. Provisional Patent Application No. 61/423,995, entitled DIRECT MEMORY ACCESS (DMA) CONTROLLED STIMULATION, filed Dec. 16, 2010, which is incorporated herein by reference.

FIELD OF THE INVENTION

Embodiments of the present invention generally relate to methods, devices and systems that are used to provide stimulation, such as, but not limited to, neurostimulation to treat pain or other conditions.

BACKGROUND OF THE INVENTION

Neurostimulation has become an accepted treatment for patients with chronic pain in their back and/or limbs who have not found pain relief from other treatments. In general, neurostimulation comprises applying an electrical current to nerve tissue in the pathway of the chronic pain. This creates a sensation that blocks the brain's ability to sense the previously perceived pain. There are two conventional forms of electrical stimulation commonly used to treat chronic pain: Spinal Cord Stimulation (SCS) and Peripheral Nerve Field Stimulation (PNFS). In SCS, electrical leads are placed along the spinal cord. A programmable implantable neurostimulator (INS) is implanted in the upper buttock or abdomen (under the skin) which emits electrical currents to the spinal cord via electrodes of the leads. Peripheral nerve field stimulation is similar to spinal cord stimulation, however peripheral nerve field stimulation involves placing the leads just under the skin in an area near to the peripheral nerves involved in pain.

A programmable INS requires circuitry for controlling the myriad of functions that are generally required to perform neurostimulation and a battery for powering such circuitry, as well as for providing the power necessary for generating neurostimulation signals. For example, a programmable INS can include an application specific integrated circuit (ASIC) for controlling the myriad of functions. However, an ASIC is relatively expensive to design, and typically requires a significant redesign whenever features are changed and/or added. For another example, a programmable INS can include an off-the-shelf central processing unit (CPU) that can be used to control the myriad of functions. This is beneficial because it provides for an off-the-shelf solution. However, if the CPU is not used in a power efficient manner, the use of the CPU can consume significantly more power than is practical, especially considering the desire to minimize the power consumed by the INS to thereby extend the useful life of the INS.

BRIEF SUMMARY OF THE INVENTION

Specific embodiments of the present invention generally relate to implantable stimulation systems, and methods for use therewith, that include direct memory access (DMA) controlled stimulation.

In accordance with an embodiment, an implantable stimulation system (e.g., an implantable neurostimulation system (INS)), comprises memory including a first table and a second table. The first table stores blocks of stimulation event data corresponding to stimulation events that are to be performed during a period of time (e.g., a 0.5 sec. or 1 sec. period of time). The second table stores blocks of next stimulation event time data corresponding to the period of time. The implantable stimulation system also includes a direct memory access (DMA) controller including a first DMA channel and a second DMA channel. The first DMA channel selectively transfers one of the blocks stimulation event data from the first table to one or more registers that are used to control stimulation events. In this manner, the DMA controller can be used to control stimulation events. Such one or more registers that are used to control the stimulation events can correspond to I/O ports of a microcontroller unit (MCU) that includes the DMA controller and the memory.

The second DMA channel selectively transfers one of the blocks of next stimulation event time data from the second table to a timer that is used to control timing associated with the stimulation events.

The implantable stimulation system also comprises a timer including a count register and a first compare register. Each of the blocks of next stimulation event time data comprises a value, which when transferred by the second DMA channel to the timer is stored in the first compare register of the timer. The count register of the timer stores a count value and increments the count value in dependence on a clock signal. The first compare register compares the value stored in the first compare register to the count value of the count register, and generates a first trigger when the value stored in the first compare register equals the count value of the count register. The first DMA channel transfers a next block of the stimulation event data from the first table to the one or more registers that are used to control stimulation events in dependence on the first trigger generated by the first compare register.

The second DMA channel transfers a next block of the next stimulation event time data from the second table to the first compare register in dependence on the first trigger signal generated by the first compare register, a trigger signal generated in response to the first DMA channel starting a transfer, or a trigger signal generated in response to the first DMA channel completing a transfer.

In an embodiment, the timer also includes a second compare register that stores a reset value. The timer compares the reset value to the count value of the count register. When the stored reset value equals the count value of the count register, the count value of the count register is reset.

In accordance with an embodiment, each of the blocks of stimulation event data corresponds to a stimulation event and includes at least a first group of bits and a second group of bits. The first group of bits specify which one of a plurality of leads, if any, is selected for the stimulation event. The second group of bits specify how the electrodes of a selected lead are connected during the stimulation event. In an embodiment, the first group of bits are transferred by the first DMA channel to a first portion of the one or more registers that correspond to I/O ports connected to circuitry that controls lead selection. Simultaneously, the second group of bits are transferred by the first DMA channel to a second portion of the one or more registers that correspond to I/O ports connected to circuitry that controls electrode configuration.

In accordance with an embodiment, the implantable stimulation system also includes a central processing unit (CPU). The CPU receives or otherwise accesses neurostimulation data that defines neurostimulation signals to be delivered via one or more leads. Based on the neurostimulation data, the CPU generates the first and second tables that are stored in the memory. After the CPU generates the first and second tables, the DMA controller controls the stimulation events for the period of time (e.g., 0.5 sec. or 1 sec.) without CPU intervention, thereby enabling the CPU to perform other tasks unrelated to performing the stimulation events and/or to enter a low-power mode during the period of time.

In accordance with an embodiment, the CPU identifies potential pulse collisions based on the neurostimulation data, and the CPU generates the first and second tables so that the identified potential pulse collisions are avoided when the DMA controller controls the stimulation events for the period of time in dependence on the first and second tables.

In accordance with an embodiment, the implantable stimulation system includes a first clock circuit and a second clock circuit, wherein the second clock circuit generates a higher frequency clock signal than the first clock circuit, which results in the second clock circuit consuming more power than the first clock circuit. The clock signal generated by the first clock circuit can, e.g., be used by the count register (of the timer) to increment the count value. The higher frequency clock signal generated by the second clock circuit is used by the CPU when the CPU is not in the low-power mode, and/or may be used by the count register to increment the count value. In accordance with an embodiment, in order to conserve power, if the clock signal generated by the lower power second clock circuit is used to increment the count register, then the first clock circuit is at least partially disabled when the CPU is in the low-power mode.

In accordance with an embodiment, based on the neurostimulation data received or otherwise accessed by the CPU, the CPU can determine whether the clock signal generated by the first clock circuit has sufficient resolution to be used as the clock signal that the count register (of the timer) uses to increment the count value, or whether the clock signal generated by the second clock circuit needs to be used as the clock signal that the count register uses to increment the count value. If the clock signal generated by the first clock circuit has sufficient resolution, then the clock signal generated by the first clock circuit is used and the second clock circuit can be at least partially disabled. If on the other hand the higher frequency clock signal generated by the second clock circuit needs to be used, then the clock signal generated by the second clock circuit is used, and the lower frequency first clock circuit can be at least partially disabled. Additionally, the first and second tables are generated by the CPU in dependence on whether the clock signal having the first frequency or the clock signal having the second frequency is used as the clock signal that increments the count register.

This summary is not intended to summarize all of the embodiments of the present invention. Further and alternative embodiments, and the features, aspects, and advantages of the embodiments of invention will become more apparent from the detailed description set forth below, the drawings and the claims.

DETAILED DESCRIPTION

Figure 1:
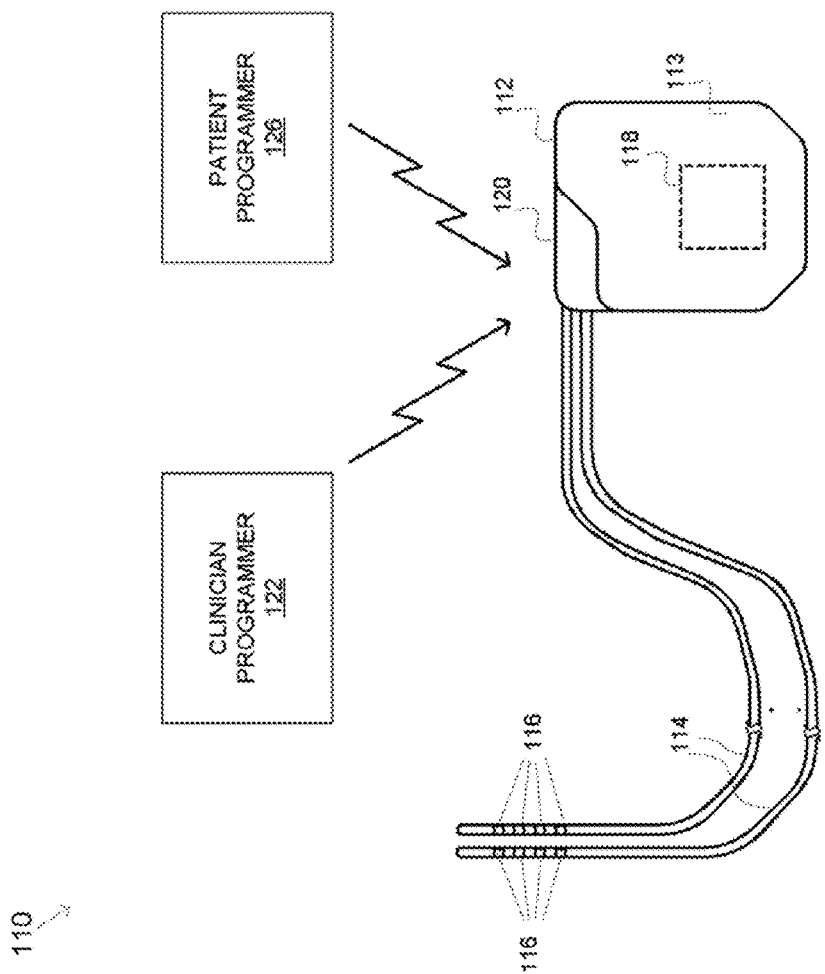
FIG. 1 illustrates an example neurostimulation system of an embodiment of the present invention.

An example neurostimulation system 110 of an embodiment of the present invention is illustrated in FIG. 1. In this embodiment, the system 110 includes an implantable neurostimulator (INS) 112, which is sometimes also referred to as an implantable pulse generator (IPG). The INS 112 is typically implantable in a subcutaneous pocket within a patient's body. One or more leads 114 are connected to the INS 112, with each lead including one or more electrodes 116. For example, four leads 114 can be connected to the INS 112, with each lead including four electrodes 116. Alternatively, more or less leads can be used, with more or less electrodes per lead. The INS 112 includes electronic circuitry 118 contained within a housing 113 (also referred to as the "case" or "can") of the INS. The electrodes 116 are electrically coupled to the electronic circuitry 118 by coupling the leads 114 to a connector 120 of the INS 112. Although not limited thereto, one or more leads 114 can be positioned so that the electrodes are disposed on or near a dorsal root or dorsal root ganglion. Additional details regarding such stimulation are provided in U.S. Pat. No. 7,450,993, entitled "Methods for Selective Stimulation of a Ganglion", and U.S. patent application Ser. No. 12/607,009, entitled "Selective Stimulation Systems and Signal Parameters for Medical Conditions", both of which are incorporated herein by reference.

The electronic circuitry 118 can be used to generate and provide an electrically stimulating signal (also referred to as a neurostimulation signal, a neurostimulation waveform, or simply a stimulation signal) to a nerve tissue via at least two of the electrodes 116, with at least one of the electrodes connected as an anode, and at least one of the electrodes connected as a cathode. Where a housing 113 of the INS 112 is electrically conductive, the housing can act as an electrode. An external programmer 122 or 126 can be used to program various stimulation parameters and/or other instructions into the electronic circuitry 118. The programmer includes a processor (or other type of controller) and memory that can store one or more code modules. The processor or other controller can execute one or more code modules to perform programming of the INS 112 based on feedback from the patient during a programming protocol. For example, the external programmer 122 or 126 can transmit instructions to the INS 112 that instruct the INS to test specific neurostimulation parameters, adjust certain parameters, and/or program certain parameters as those to be used by the INS for chronic treatment of pain. The external programmer 122 or 126 may include (or be coupled to) a telemetry device that communicates with the electronic circuitry 118 via radio frequency or other wireless signals. Regardless whether the telemetry device is within the programmer or coupled to the programmer, the programmer can be said to include telemetry circuitry. The INS 112 can similarly include a processor (or other type of controller) that can execute code modules stored in memory of the INS.

There are generally two types of programmers, both of which can be handheld and capable of wireless communication with the INS 112. The programmer represented by block 122, which is often referred to as a "clinician programmer", may be used by a representative of the INS manufacturer, a clinician, a physician and/or other medical personnel (collectively referred to hereafter as a "programming person"). Block 126 represents another type of programmer, which is often referred to as a "patient programmer," which is primarily intended to be controlled by the patient within which the INS 112 is implanted.

A set of stimulation parameters that define how neurostimulation (also referred to simply as stimulation) is to be delivered using a specific lead can be referred to as a "lead set" since the set defines the stimulation therapy to be delivered to a patient via a lead. One or more "lead sets" can be grouped together into a group of sets of stimulation parameters, which can be referred to as a "simulation set". One set of stimulation parameters (i.e., one "lead set") may be useful for treating a condition in one location of the body of the patient, while a second set of stimulation parameters (i.e., a second "lead set") may be useful for treating a condition in a second location of the body. If both such "lead sets" are grouped together into the same "stimulation set", then treatment can be delivered to both the first and second locations of the body when that stimulation set is selected. It is also possible the more than one "lead set" grouped into the same "stimulation set" can be used for delivering treatment to a common location of the body.

The data for each "lead set" includes lead information, electrode configuration information and stimulation waveform information. More specifically, in an embodiment the data for each "lead set" specifies one of the leads, how each of the multiple electrodes (e.g., four electrodes) of the lead is to be configured (i.e., as an anode electrode, a cathode electrode, or an inactive electrode), and specifies an amplitude, a pulse width and a repetition rate of the stimulation waveform to be delivered using that lead. In an embodiment, data for each "stimulation set" specifies which one or more "lead set" (e.g., up to four lead sets) are included as part of the "stimulation set". For example, if there are 12 "lead sets" (i.e., lead set 1, lead set 2, ... lead set 12), a "stimulation set" can include lead set 2, lead set 5, lead set 7 and lead set 11. During a period of time that a specific "stimulation set" is selected/active, stimulation can be delivered using all four leads (although, at any moment in time during that period it may be that stimulation can only be delivered using one of the leads). More than one lead set can specify the same lead (i.e., can have the same lead information), yet have different electrode configuration information and/or different stimulation waveform information. For example, lead set 1, lead set 2, and lead set 3 can each specify different ways that stimulation can be delivered using the same lead. In some embodiments, two lead sets specifying the same lead can not be grouped into the same stimulation set.

In accordance with an embodiment, an external programmer (e.g., a clinical programmer 122) wirelessly transmits data for multiple "lead sets" (e.g., up to twelve lead sets) and multiple "stimulation sets" (e.g., up to four stimulation sets) to the INS 112. The data for one or more "lead set" can also be referred to as lead set data, and the data for one or more "stimulation set" can also be referred to as stimulation set data. More generally, data that is transmitted from an external programmer to the INS 112, which is used by the INS to generate stimulation signals, can be referred to as neurostimulation data. Such neurostimulation data can include lead set data and stimulation set data, but is not limited thereto. In other words, there are other ways to organize information that defines neurostimulation to be delivered by an INS other than those ways described above, and such other ways can also be used to generate neurostimulation data, while being within the scope of the present invention. Nevertheless, for the remainder of this discussion it will be assumed that an external programmer 122 or 126 is used to program multiple "lead sets" (e.g., up to twelve lead sets) and multiple "stimulation sets" (e.g., up to four stimulation sets) into the INS 112.

When the INS 112 receives the lead set data and the stimulation set data from the external programmer, the INS 112 stores lead set data and stimulation set data in a portion of memory (e.g., 320), such as, but not limited to, in non-volatile memory (e.g., flash). Also stored in memory (e.g., 320) is a "current stimulation set" parameter, which specifies which "stimulation set" is currently active/selected. Additional details of how the neurostimulation data (e.g., lead set data and the stimulation set data) stored within the INS 112 can be used by the INS 112 to generate neurostimulation signals is provided below.

Electronic Circuitry 118

Figure 2:
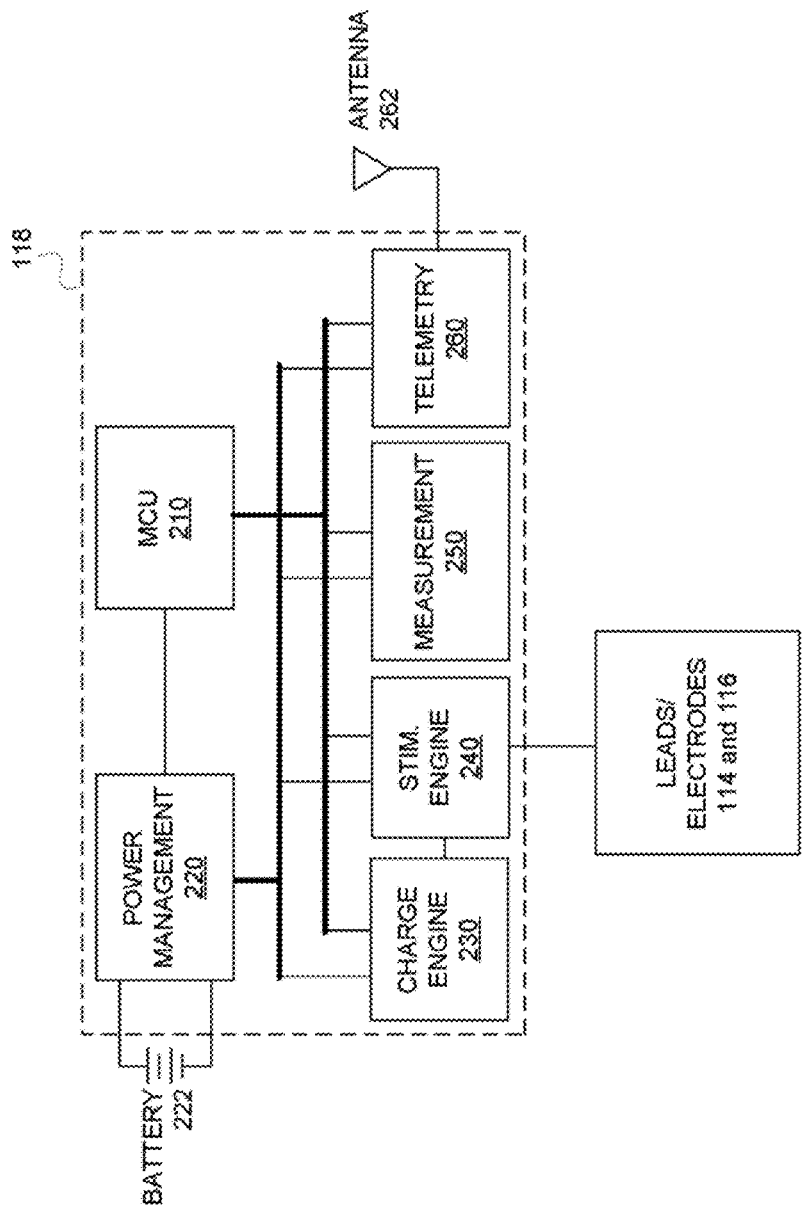
FIG. 2 is a high level block diagram of the electronic circuitry of the implantable neurostimulator (INS) shown in FIG. 1.

FIG. 2 will now be used to describe details of the electronic circuitry 118 of the INS 112, according to an embodiment of the present invention. Referring to FIG. 2, the INS 112 is shown as including a microcontroller unit (MCU) 210, power management circuitry 220, charge engine circuitry 230, stimulation engine circuitry 240, measurement circuitry 250 and telemetry circuitry 260. The MCU 210, which includes a central processing unit (CPU), can control many of the functions of the INS, as will be described in additional detail below, e.g., with reference to FIGS. 3 and 4.

The power management circuitry 220 is shown as being connected to a battery 222, and is used to generate the appropriate voltage and/or current levels for powering the various other circuitry. Accordingly, the power management circuitry 220 can include DC-DC converters, such as, but not limited to, boost and/or buck converts. Additionally, or alternatively, the power management circuitry 220 can include other types of voltage generators. The power management circuitry 220 can also monitor the remaining battery life of the battery 222, so that a patient and/or medical personnel can be informed when the battery 222 needs to be replaced, or possibly recharged.

While not shown in FIG. 1 or 2, the INS 112 can include control capacitors that store charges used to maintain, adjust and/or otherwise control charges stored by therapy output capacitors, wherein the therapy output capacitors are used to deliver stimulation to patient tissue. The charge engine 230 can include and be used to charge up such control capacitors. The charge engine 230 can also be used to sample the voltages stored on the therapy storage capacitors to make sure the appropriate charges are maintained and/or changed as necessary. Exemplary details of the charge engine 230 are shown in and described with reference to FIG. 4A.

The stimulation engine 240 is shown as being electrically connected to one or more leads 114, wherein each lead includes at least two electrodes 116. For the remainder of this discussion, unless stated otherwise, it will be assumed that the implantable system 110 includes four leads, each of which includes four electrodes. However, more or less leads, and more or less electrodes per lead are possible, and within the scope of the present invention. The stimulation engine 240 can be used to select specific leads and configure electrodes of selected leads. Exemplary details of the stimulation engine 240 are shown in and described with reference to FIG. 4B.

The measurement circuitry 250 can be used, e.g., to measure lead impedance, lead output current, lead output voltage, battery voltage and battery current, but is not limited thereto.

The telemetry circuit 260 can be a radio frequency (RF) transceiver electrically connected to an antenna 262, e.g., by a coaxial cable or other transmission line. The telemetry circuit 260 can include any well known circuitry for transmitting and receiving signals via the antenna 262 to and from a telemetry transceiver of a clinical programmer and/or patient programmer (e.g., 122 and/or 126).

As will be described in more detail below, the electronic circuitry 118 can be used to generate neurostimulation signals, and control switches (of the electronic circuitry 118) to couple stimulation energy to selected electrodes of a selected lead. The stimulation pulses can be generated in accordance with parameters specified by neurostimulation data stored within memory (e.g., memory 320 in FIG. 3). Exemplary programmable parameters that can be specified include the pulse amplitude, pulse width, and pulse rate (also known as repetition rate or frequency) for a neurostimulation waveform (also known as a neurostimulation signal), as was mentioned above. Additionally, the electronic circuitry 118 can control the switches to select different electrode configurations for delivery of stimulation.

MCU 210

Figure 3:
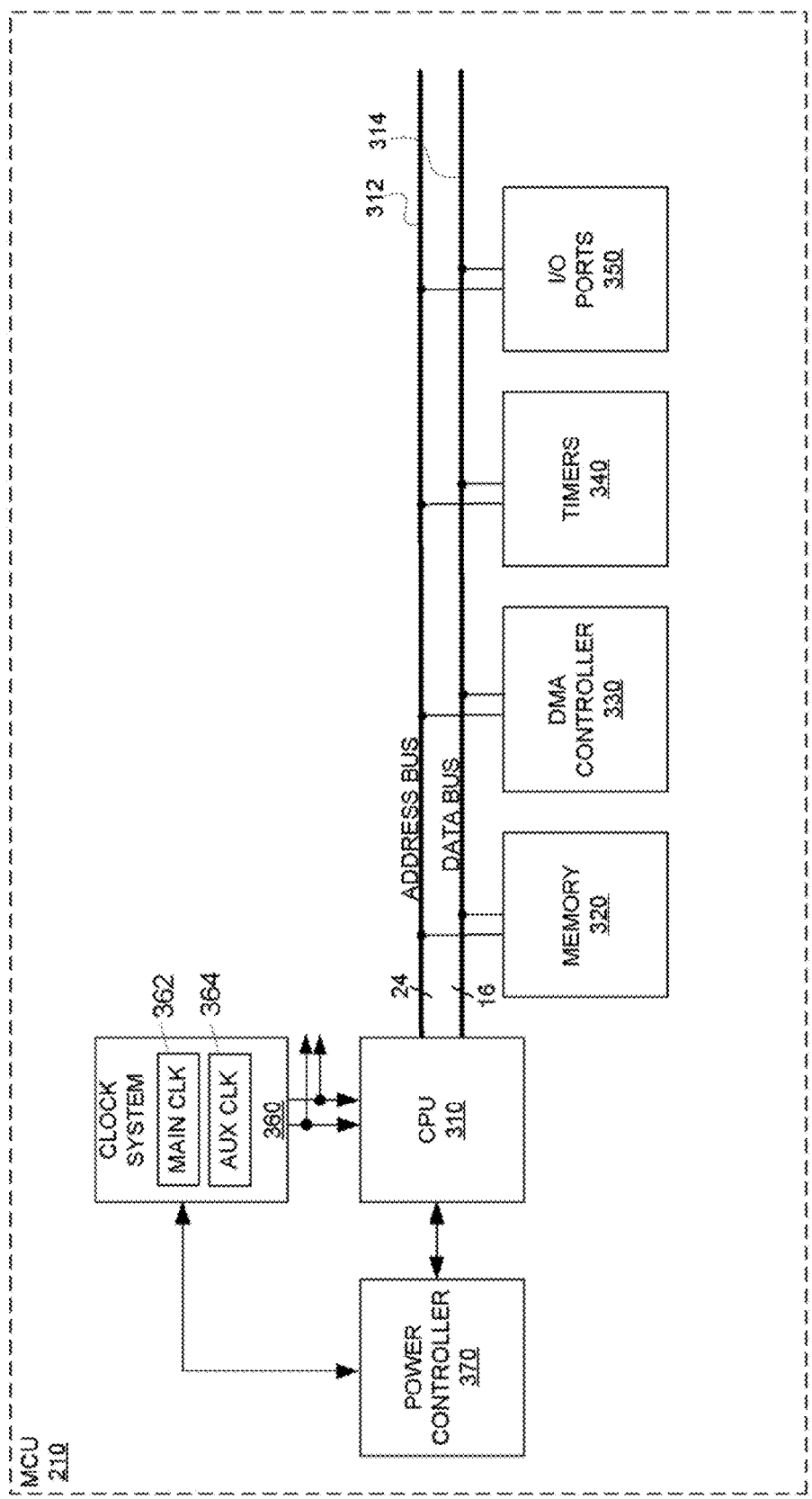
FIG. 3 illustrates exemplary components of the microcontroller (MCU) shown in FIG. 2, which can be used for controlling neurostimulation.

FIG. 3 illustrates exemplary components of the microcontroller (MCU) 210, which can be used, in accordance with embodiments of the present invention, for controlling neurostimulation, such as, but not limited to, controlling stimulation delivered to or adjacent a patient's spinal cord or a portion thereof, including, but not limited to, stimulation of a dorsal root or dorsal root ganglion. Referring to FIG. 3, the MCU 210 is shown as including a central processing unit (CPU) 310 connected to an address bus 312 and a data bus 314. The address bus 312 can be a 24 bit bus, but is not limited to thereto. The data bus can be a 16 bit bus, but is not limited thereto. Also connected to the address and data busses 312 and 314 are memory 320, a direct memory access (DMA) controller 330, timers 340 and input/output (I/O) ports 350. A DMA controller is sometimes referred to as a Data Transfer Controller. Also shown in FIG. 3 is a clock system 360 that can generate clock signals having different frequencies that can be provided to the CPU 310 and other components of the MCU 210 and/or other components of the electronic circuitry 118. Additionally, a power controller 370 is shown, which can control when the CPU 310 enters low-power mode, and/or can control whether and when portions of the clock system 360 are at least partially disabled (to save power). The power controller 370 can also be referred to as a power management module (PMM).

The memory 320 can include volatile and/or non-volatile memory including, but not limited to, RAM, ROM, NVRAM, EEPROM, flash memory, and the like. As will be described with reference to FIG. 5, the memory 320 can store data in multiple tables. Such tables can be generated, e.g., by the CPU 310, based on instructions stored in code modules and based on neurostimulation data received from an external programmer. Additionally, as will be described with reference to FIG. 5, after the tables are generated by the CPU 310 and stored in the memory 320, the DMA controller 330 can transfer data from the tables to one of the timers 340 and I/O ports 350 without, or with very little, intervention by the CPU 310.

An advantage of having all the components shown in FIG. 2 be within a single MCU is that all such components can be provided by a single integrated circuit (IC) chip. Nevertheless, it is also within the scope of the present invention that all or portions of the components shown in FIG. 3 are not located within a MCU chip. For example, the CPU 310 can be provided by one chip, the DMA controller 340 by another chip, etc.

In accordance with specific embodiments of the present invention, at least some of the I/O ports 350 are configured as output ports (as opposed to input ports) and are used for stimulation control, and thus, these ports can also be referred to herein as stimulation control ports 350. In such embodiments, one or more registers, or portions thereof, are associated with the I/O ports to store bits (e.g., high or low logic level bits) that are used to control circuitry connected to the I/O ports. Exemplary circuitry that can be connected to the I/O ports (and thereby controlled by bits written to those ports) include the charge control engine circuitry 230 and the stimulation engine circuitry 240, but is not limited thereto.

As mentioned above, the clock system 360 can generate clock signals having different frequencies that can be provided to the CPU 310 and other components of the MCU 210. For example, the clock system 360 can include main clock circuitry 362 that generates a relatively high frequency (e.g., 100 kHz) clock signal. The clock system 360 can also include auxiliary clock circuitry 364 that generates a lower frequency (e.g., 32.768 kHz) clock signal and thereby consumes less power than the main clock circuitry 362. The higher frequency clock signal generated by the main clock circuitry can be used, e.g., by the CPU 310 while the CPU is performing tasks that are to be performed as fast as possible. To conserve power, the main clock circuitry 362 can be at least partially disabled when appropriate, and the lower frequency clock signal generated by the auxiliary clock circuitry 364 can be used, e.g., for time keeping functions, or for performing tasks that if performed using the lower frequency clock signal do not adversely affect performance. To conserver power, it is also possible to at least partially disable the auxiliary clock circuitry 364 when the lower frequency clock signal is not needed. The power controller 370, which can also be referred to as a power management module (PMM), can control such disabling of portions of the clock circuitry.

Additional details of the memory 320, the DMA controller 330, one of the timers 340 and the stimulation control ports 350 are described below with reference to FIG. 5. However, a brief description of the charge engine circuitry 230 and the stimulation control circuitry 240, according to an embodiment, are first described with reference to FIGS. 4A and 4B.

Charge Engine 230

Figure 4A:
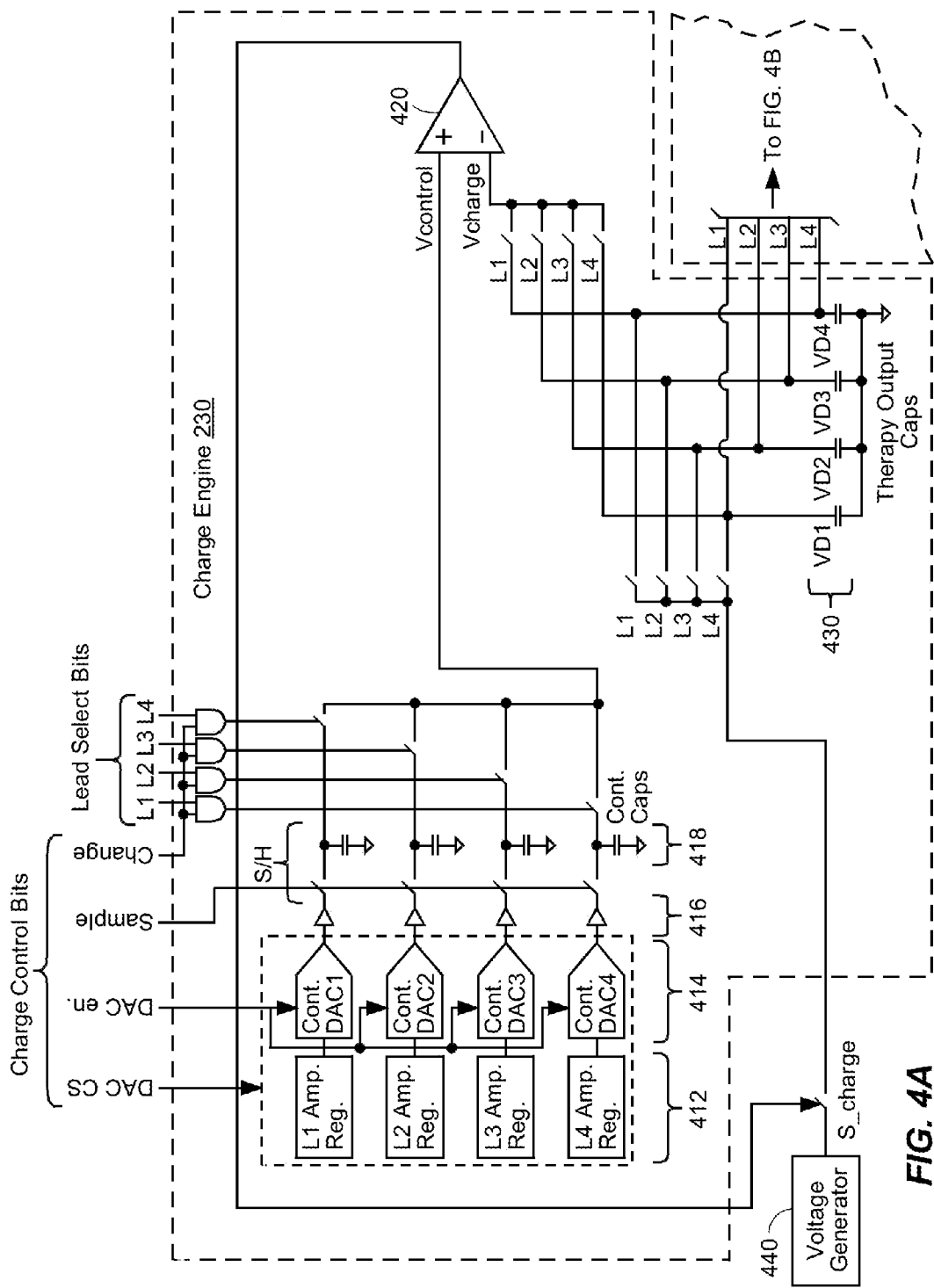
FIGS. 4A and 4B illustrate exemplary details of the charge engine and the stimulation engine shown in FIG. 2.

Exemplary details of the charge engine circuitry 230 (also referred to simply as the charge engine) will now be described with reference to FIG. 4A. Referring to FIG. 4A, the charge engine is shown as including a plurality (four in this example) of control digital-to-analog converters (DACs) 414, each of which is driven by a corresponding register 412. In an embodiment, each of the registers 412 stores a digital amplitude value that is used to define the amplitude of each phase of a biphasic pulse for delivery via one of the leads. Exemplary biphasic pulses are shown in and described with reference to FIG. 6.

The digital amplitude values stored in the registers 412 can be defined by the lead set information specified by a clinical programmer 122, and may thereafter be adjusted using a user interface (e.g., an up/down button, or the like) on a patient programmer 126. As will be described below, the CPU 310 can write amplitude values to the amplitude registers 412, e.g., based on which "stimulation set" is activated/selected at the time (e.g., as specified by a "current stimulation set" parameter stored in memory).

In FIG. 4A, the L1 Amp. Reg. 412, the Cont. DAC1 414 and corresponding sample-and-hold (S/H) circuitry 416 can be considered a first charge control channel. Thus, in FIG. 4, four charge control channels are shown, one for each of the leads L1, L2, L3 and L4.

When enabled, each DAC 414 generates an analog output voltage proportional to the digital value provided to the input of the DAC by the corresponding register 412. At the output of each DAC is a buffer 416 that isolates that DAC from circuitry downstream of the buffer. When the sample bit of the charge control bits is active, the sample switches (of the S/H circuitry 416) are closed, causing the control capacitors 418 to be charged such that they store a voltage dependent on the output of the corresponding DAC 414.

The charge engine 230 is also shown as including a therapy output capacitor 430 for each of the leads L1, L2, L3 and L4. The voltage stored by each therapy output capacitor 430 can be used to generate the biphasic stimulation pulses for one of the leads, as will be explained in more detail below.

The charge engine 230 is also shown as including a comparator 420 that is used to selectively compare the voltage stored by one of the control capacitors 418 to the voltage stored by a corresponding one of the therapy output capacitors 430. The output of the comparator 420 is used to control a switch (S_charge) that when closed increases the charge on a therapy output capacitor 430, and when opened allows the charge on a therapy output capacitor 430 to slowly discharge. The voltage generator 440 shown in FIG. 4A can be considered part of the power management circuit 220.

The registers 412 can be connected to the address bus 312 and data bus 314 shown in FIG. 3, thereby enabling the CPU to write to the registers 412. Alternatively, the registers 412 can be written to using a serial bus connected between the registers and the CPU. The digital amplitude values stored in the registers 412 may also be modified via a user interface, e.g., an up/down button or the like, on a clinical or patient programmer 122 or 126, as mentioned above. When such a user interface is controlled by a user, the programmer can wirelessly transmit instructions to the INS 112 to increase or decrease a value in one of the registers 412. In an embodiment, one or more charge control bits can cause a CPU interrupt that triggers the CPU to change the digital amplitude values stored in the registers 412.

Stimulation Engine 240

Figure 4B:
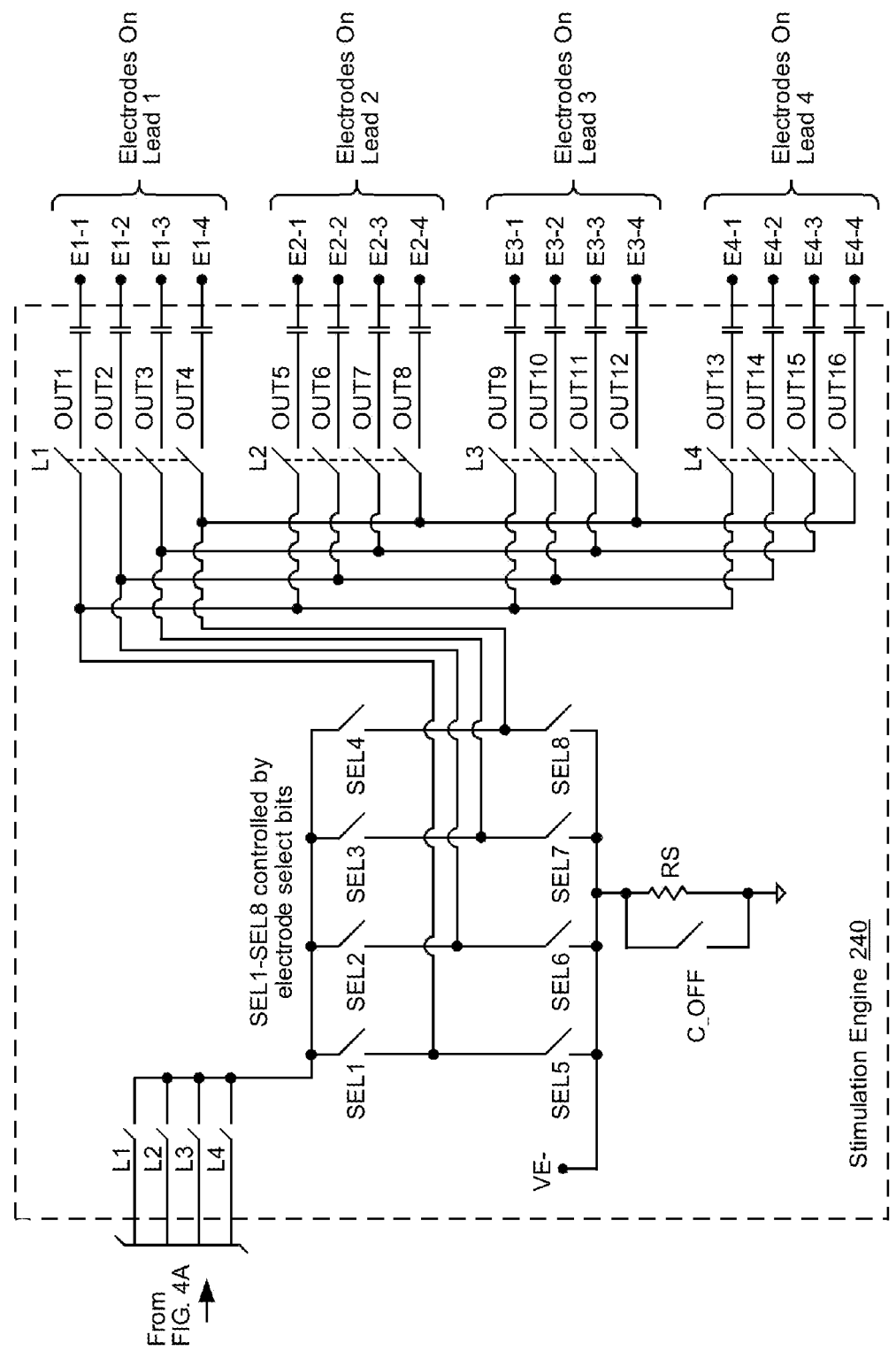

Exemplary details of the stimulation engine circuitry 240 (also referred to simply as the stimulation engine) will now be described with reference to FIG. 4B. Referring to FIG. 4B, the stimulation engine 240 is shown as including electrode switches SEL1-SEL8 that are controlled by electrode configuration bits (e.g., 8 bits) of stimulation event data. In the lower right hand corner of FIG. 4B, the stimulation engine 240 is also shown as including four ganged together switches for each lead (used to control whether each individual lead is selected) that are controlled by lead select bits (e.g., 4 bits) of stimulation event data. In an embodiment, to generate a stimulation pulse of a stimulation signal, one of the leads L1, L2, L3 and L4 is selected (using the lead select bits), at least one of the electrodes is configured as an anode by using switches SEL1-SEL4 to connect electrode(s) to one of the therapy output capacitors 430, and at least one of the one of the electrodes is configured as a cathode by using switches SEL5-SEL8 to connect other electrode(s) to VE-.

As will be appreciated from the description below, many embodiments of the present invention that relate to DMA controlled neurostimulation can also be performed using alternative circuitry that performs the functions of the charge engine 230 and stimulation engine 240. In other words, embodiments of the present invention that relate to DMA controlled neurostimulation should not be limited to use with the circuitry shown in FIGS. 4A and 4B.

DMA Controlled Neurostimulation

As explained above, in a specific embodiment the INS 112 can store a plurality (e.g., up to twelve) "lead sets" and a plurality (e.g., up to four) "stimulation sets" in memory (e.g., 320). Each "lead set" can be associated with one of a plurality (e.g., four) leads, and can specify whether the lead is enabled, how each of the four electrodes of the lead (if the lead is enabled) is configured (i.e., as an anode, as a cathode, or inactive), and the amplitude, pulse width and repetition rate of stimulation to be delivered via that lead. Each "stimulation set" can group together a plurality (e.g., up to four) "lead sets" such that more than one "lead set" can be active during the same period of time (e.g., they can essentially be time multiplexed for a period of time). Also stored in the memory can be a "current stimulation set" parameter, which specifies the "stimulation set" is currently active/selected.

In accordance with an embodiment, the "lead set" data and "stimulation set" data (and more generally, the neurostimulation data) stored in the memory 320 (e.g., in flash) are accessed by the CPU 310 of the MCU 210 of the INS 112. Based on which "stimulation set" is activated/selected at the time (as specified by the "current stimulation set" parameter), the CPU 310 generates and stores stimulation event data, and next stimulation event time data, which can be stored as two look up tables (LUTs) in the memory 320 (e.g., in RAM). Examples of such LUTs are labeled 522 and 524 in FIG. 5. In accordance with an embodiment, every time a different "stimulation set" is activated/selected (e.g., via an external programmer), the two LUTs are regenerated to correspond to the newly activated/selected "stimulation set". Based on which "stimulation set" is activated/selected at the time (e.g., as specified by the "current stimulation set" parameter), the CPU 310 can also write amplitude values to the amplitude registers 412 (see FIG. 4A).

Additional details of how the DMA controller 330 can be used to generate neurostimulation signals, in accordance with an embodiment of the present invention, will now be described. Referring to the schematic diagram of FIG. 5, the memory 320 includes a portion of memory 522 that stores stimulation event data, and a portion of memory 524 that stores next stimulation event time data. The stimulation event data stored in the portion of memory 522 can be used to define N stimulation events. In accordance with an embodiment, each of the N stimulation events is defined by lead select bits (e.g., 4 bits), electrode configuration bits (e.g., 8 bits) and charge control bits (e.g., 4 bits). Thus, for this example, because each stimulation event can be defined by 2 bytes (i.e., 4+8+4=16 bits=2 bytes), the stimulation event data stored in the portion of memory 522 can be 2*N bytes of data. The next stimulation event timing data stored in the portion of memory 524 can be used to define the timing of N stimulation events, e.g., with each next stimulation event timing data timing defined by 16 bits (i.e., 2 bytes). Thus, for this example, the next stimulation event time data stored in the portion of memory 524 can be 2*N bytes of data. Additional details of the stimulation event data, including details of lead select bits, electrode configuration bits and charge control bits, are described below.

The portion of memory 522 that stores stimulation event data can be a first table, e.g., a first look up table (LUT) that includes N stimulation event entries, with each entry being a block of data. Similarly, the portion of memory 524 that stores next stimulation event time data can be a second table, e.g., a second LUT, that includes N next stimulation event time entries, with each entry being a block of data.

The DMA controller 330 includes at least two DMA channels, including a DMA channel 532 (which can also be referred to as the stimulation event DMA channel) and a DMA channel 534 (which can also be referred to as the next stimulation event time DMA channel). Each DMA channel can be used for copying (also referred to as transferring) a block of memory from one location to another without subjecting the CPU 310 to the heavy overhead the CPU 310 would experience if the CPU 310 were responsible for such copying/transfers. This frees the CPU 310 to perform other tasks, or to go into a low-power mode.

The timer 340 is shown as including a timer count register 542 and two timer compare registers 544 and 546 (also known as capture compare registers). The timer compare register 544 can also be referred to as an event timer compare register, since it is used to trigger stimulation events. The timer compare register 546 can also be referred to as a reset timer compare register, since it is used to reset the timer counter register 542. The timer count register 542 receives a clock (CLK) signal, and is incremented once per cycle of the CLK signal. The contents of the timer count register 542 are compared to the contents of the event timer compare register 544 and to the contents of the reset timer compare register 546. In accordance with an embodiment of the present invention, when the contents of the timer count register 542 and the event timer compare register 544 are equal, the timer 340 triggers both of the DMA channels 532 and 534 (as represented by dashed lines 547 and 548). Alternatively, the timer 340 can trigger the DMA channel 532 when the contents of the timer count register 542 and the event timer compare register 544 are equal (as represented by dashed line 547), and the DMA channel 532 (upon starting or completing a transfer) can in turn trigger the DMA channel 534.

In accordance with an embodiment of the present invention, when the contents of the timer count register 542 and the reset timer compare register 544 are equal, the timer count register 542 is reset to zero (or some other predetermined value), as represented by dashed line 549. In accordance with an embodiment, when the timer count register 542 is reset an interrupt is sent to the CPU 310. In an alternative embodiment, when the DMA channel 532 transfers the last block of data in the portion of memory 522 that stores stimulation event data, the timer count register 542 is reset to zero (or some other predetermined value) and an interrupt is sent to the CPU 310.

The DMA channel 532, when triggered, transfers (i.e., copies) a block of memory from the portion of memory 522 (that stores stimulation event data) to registers associated with the stimulation control ports 350. A pointer associated with the DMA channel 532 is incremented each time the DMA channel 532 is triggered, so that the next time the DMA channel 332 is triggered the next block of stimulation event data is transferred to the registers associated with the stimulation control ports 350. The pointer is incremented by the amount of data used to define a stimulation event, which in this example is 2 bytes. After the pointer points to the last block in the portion of memory 522 (e.g., Stim Event N−1 in FIG. 5) the pointer is reset so that it again points to the first block in the portion of memory 522 (e.g., Stim Event 0 in FIG. 5).

Each block of stimulation event data is used to define one or more stimulation events. A stimulation event, as the term is used herein, refers to any change of the state of circuitry that is controlled to occur at a point in time. For example, a stimulation event can change the state of circuitry that controls which one of a plurality of leads is selected, which electrode(s) of a selected lead is/are connected as an anode (if any), which electrode(s) of a selected lead is/are connected as a cathode (if any), and which electrode(s) of a selected lead is/are inactive, i.e., neutral or off (if any). For another example, a stimulation event can cause the charging or discharging of one or more specific capacitors. Depending on implementation, and depending on the specific stimulation event, once a stimulation event is initiated, the stimulation event may time out on its own, or it may end when a next stimulation event begins. Multiple stimulations events can be initiated simultaneously, e.g., a lead can be selected at the same time that the electrodes on that lead are configured.

When triggered, the DMA channel 534 transfers (i.e., copies) a block of memory from the portion of memory 524 (that stores next stimulation event time data) to the event timer compare register 544 of the timer 340. A pointer associated with the DMA channel 534 is incremented each time the DMA channel 534 is triggered, so that the next time the DMA channel 334 is triggered the next block of next stimulation event time data is transferred. The pointer is incremented by the amount of data used to define a next stimulation event time, which in this example, is 2 bytes. After the pointer points to the last block in the portion of memory 524 (e.g., Time 0 in FIG. 5) the pointer is reset so that it again points to the first block in the portion of memory 524 (e.g., Time 1 in FIG. 5).

Referring to the portion of memory 524 (that stores next stimulation event time data), the value of Time N−1 is greater than the value of Time N−2, . . . which is greater than Time 4, which is greater than Time 3, which is greater than Time 2, which is greater than Time 1. Thus, as the pointer changes from pointing to one block to the next block, the contents of the timer compare register will keep being increased, until Time 0 is reached. In this manner, the time (stored in the timer compare register 544) at which the timer 340 is to generate its next trigger signal(s) is repeatedly updated. In an alternative embodiment, the portion of memory 524 (e.g., the table 524) can store delta time values indicative of the length of time until the next event, and each time a new next stimulation event time data value is copied into the event time compare register 544 by the DMA controller 530 the time count register 522 can be reset (or, instead of resetting the time count register 522, the next stimulation event time data value can be added to the value in the event time compare register).

Assume for simplicity that the CLK signal (provided to the timer count register 542) is a 50 kHz clock signal, and that a value of 50,000 is stored in the reset timer compare register 546. In this example, the timer count register 542 counts from 0 to 50,000 (i.e., from binary bits 0000000000000000 to binary bits 1111010000100100000) during a 1 second time period, at the end of which the timer count register 542 is reset to 0, and the counting from 0 to 50,000 repeats every 1 second, which is repeated every 1 second. Thus, in this example, the portion of memory 522 that stores stimulation event data, and the portion of memory 524 that stores next stimulation event time data, stores a 1 second time period worth of stimulation information. This time period can be reduced or increased by changing the value stored in the timer reset register 546 and/or changing the frequency of the CLK signal. For example, 0.5 seconds worth of stimulation information can be stored in the portion of memory 522 that stores stimulation event data, and the portion of memory 524 that stores next stimulation event time data, a value of 50,000 can be stored in the timer reset register 546, and a 100 kHz CLK signal can be used to increment the timer count register 452. These are just exemplary CLK frequencies and exemplary values that can be stored in the reset timer compare register 546, which are not meant to be limiting. As can be appreciated from this description, through selection of the value to be stored in the reset timer compare register 546 and/or the CLK frequency, almost any time period worth of data can be stored in the portions of memory 522 and 524. In an embodiment, rather than actively resetting the time count register 542 at the end of each period's worth of time (e.g., at the end of each 1 second's worth of time), the stimulation event data and the next stimulation event time data (stored in the portions of memory 522 and 524) can be generated for a period of time that will result in the timer count register 542 wrapping around to zero at the end of each period's worth of time. For example, assuming the timer counter register is a 16 bit counter, after the timer count register 542 counts from binary bits 0000000000000000 to binary bits 1111111111111111 (which corresponds to decimal 65535), the next value of the timer count register 542 will automatically be 0000000000000000. Assuming for simplicity that the CLK signal provided to the time count register is a 65,535 Hz clock, then the 16 bit timer count register 542 would automatically reset at the end of each 1 second's worth of time. In such an embodiment, there would be no need for the CPU 310 to restart the DMA channels each period of time. For the remainder of this discussion, for simplicity, it is assumed that the CLK signal is a 50 kHz clock signal, and that a value of 50,000 is stored in the timer reset register 546, resulting in a 1 second time period worth of stimulation information being stored in the portions of memory 522 and 524.

As was explained above, the portions of memory 522 and 524 store blocks of data that can be used to generate a period of time's worth (e.g., 1 second's worth) of a neurostimulation signal. In accordance with an embodiment, this period of time's worth of the neurostimulation signal is repeatable, so that neurostimulation can be delivered for as long a period as is desired. In other words, the period of time's worth (e.g., 1 second's worth) of neurostimulation can be repeated indefinitely, e.g., until turned off by a patient or programming person, until a different stimulation set is selected/activated by a patient or programming person, or until changed by a programmed treatment schedule. It is noted that if the portions of memory 522 and 524 store blocks of data used to generate 1 second's worth of a stimulation events, and if the frequency of the CLK signal is an integer number of Hz, then it can be ensured that the stimulation events can exactly repeat each 1 second's worth of time. If the portions of memory 522 and 524 store blocks of data used to generate 0.5 second's worth of stimulation events, then the frequency of the CLK signal would need to be an even integer number of Hz for it to be ensured that the stimulation events can exactly repeat each 0.5 second's worth of time. In other words, when selecting the CLK frequency, there should be consideration of the period of time's worth of data stored in the portions of memory 522 and 524.

Figure 5:
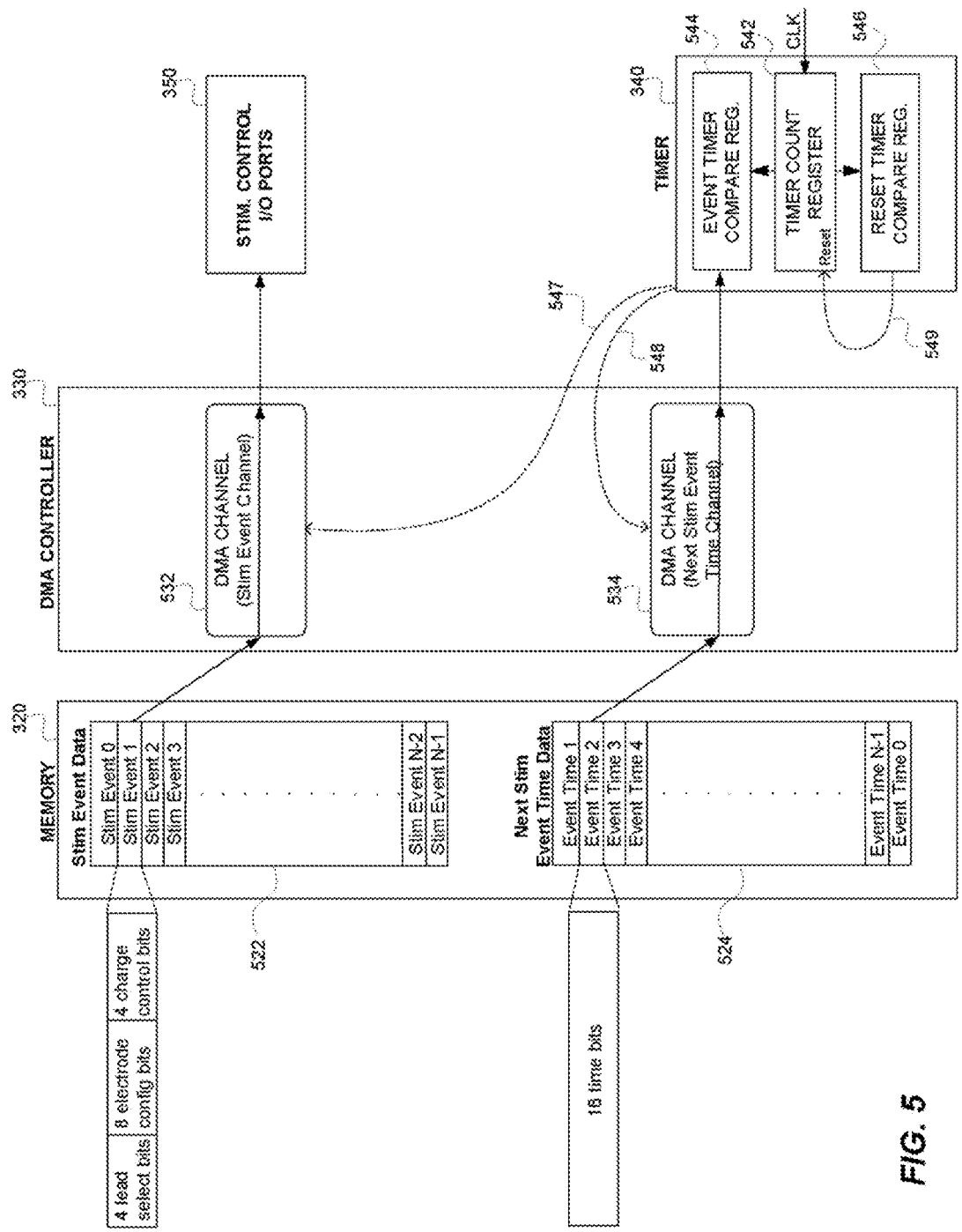
FIG. 5 illustrates how the DMA controller shown in FIG. 2 can be used to generate neurostimulation signals, in accordance with an embodiment of the present invention.

As shown in FIG. 5, N blocks of stimulation event data are stored in the portion of memory 522, and N blocks of next stimulation event time data are similarly stored in the portion of memory 524. The order for storing the N blocks in the portion of memory 522 is stimulation event 0, stimulation event 1, stimulation event 2, stimulation event 3 . . . stimulation event N-2, with the last entry being stimulation event N-1; while the order of the N blocks stored in the portion of memory 524 is next stimulation event time 1, next stimulation event time 2, next stimulation event time 3, next stimulation event time 4 . . . next stimulation event N-1, with the last entry being next stimulation event time 0. The tables are stored this manner so that as the current event data is transferred (because the event trigger time has been reached), the next event trigger time will also be simultaneously or almost simultaneously loaded into the event time comparator.

Since one DMA channel can only transfer data to one destination, in certain embodiments two tables and two DMA channels are used to transfer both stimulation event data and next stimulation event timing data, with one of the DMA channels being used to transfer the stimulation event data to I/O ports 350, and the other being used to transfer next stimulation event timing data to a register 544 of a timer 340.

In summary, in accordance with an embodiment DMA controller 330 accesses LUTs 522 and 524 to control lead selections, electrode configurations and the stimulation signal waveforms. The DMA channel 532 is used to copy stimulation event data from the stimulation event data LUT 522 to I/O ports 350 of the MCU, and the DMA channel 534 that is used to copy next stimulation event timing data from the next stimulation event timing data LUT 524 to the compare register 544 of the timer 340 of the MCU 210. The data copied to the I/O ports 350 is used to control switches and logic circuitry that control lead selections, electrode configurations, and waveform amplitude transitions. Examples of such circuitry were described above with reference to FIGS. 4A and 4B. The timing data copied to the compare register 544 of the timer 340 is used to control when the next block of the stimulation event data is to be copied from the stimulation event data LUT 522 to I/O ports 350 of the MCU 210, as well as when the next block of next stimulation event timing data is to be copied from the next stimulation event timing data LUT 524 to the compare register 544 of the timer 340. Software pointers are incremented based on the triggers and are used to identify which block of each LUT is to be copied using the DMA channels 532 and 534. In the above described manner, stimulation can be delivered that corresponds to a selected/activated "stimulation set".

In accordance with an embodiment, the CPU 310 generates the LUTs 522 and 524 so that pulse collisions do not occur (e.g., so that a pulse is being delivered via only one lead at a time). For example, if the stimulation frequency (also referred to as pulse repetition rate) to be delivered using one lead is 40 Hz, and the stimulation frequency to be delivered using another one of the leads is 42 Hz, there will be times in which both leads should receive a pulse at the exact same time from the stimulation engine 240. If the stimulation engine 240 can only deliver one pulse to one lead at a time, the CPU 310 needs to decide which lead should receive its pulse first, and which lead should receive its pulse second, thereby avoiding a "collision". Because the CPU 310 makes these decisions in advance (e.g., whenever the device is turned on, or a new "stimulation set" is activated/selected), the CPU 310 does not need to make these decisions on the fly (i.e., in real time) every time a potential collision is about to occur. This frees up the CPU 310 significantly to do other tasks or switch to a low power mode, thereby allowing the CPU to perform its other tasks much faster, and significantly reducing power consumption. The CPU 310 can use a scheduling algorithm defined by a software module to decide when pulses are to be delivered via each lead. Continuing with the example where the stimulation frequency to be delivered using one lead is 40 Hz, and the stimulation frequency to be delivered using another one of the leads is 42 Hz, the leads will still deliver, respectively, 40 pulses and 42 pulses per second, but certain pulses may be moved slightly backward or forward in time to avoid collisions.

The "collisions" corresponding to one period of time (e.g., 1 second of time) repeat each following period of time (e.g., each following second). Accordingly, once the collisions are dealt with, i.e., avoided, for the period of time (e.g., 1 second of time), they are dealt with for all repetitions of the period of time without consuming further CPU processing.

It is noted that some stimulation events (for which data is stored in the memory 320) can cause charging of capacitors, sampling of charges stored by capacitors and/or the like. Such charging and/or sampling stimulation events can be used to prepare for delivering a next stimulation pulse of a stimulation waveform, rather than for delivering an actual stimulation pulse. During such charging and/or sampling stimulation events, which can be controlled using the charge control bits, and which may occur between delivery of actual stimulation pulses, it is possible that none of the leads be selected (i.e., the lead select bits can cause no lead to be selected). Also, during such charging and/or sampling stimulation events, it is possible that no electrode is connected as an anode, and no electrode is connected as a cathode (e.g., all electrodes may be neutral, i.e., inactive). For a more specific example, it is possible that an entry in the stimulation event data table 522 includes 4 lead select bits (e.g., bits 0000) that cause no lead to be selected, and 8 electrode select bits (e.g., bits 00000000) that cause no electrode to be connected as an anode and no electrode to be connected as a cathode, and 4 charge control bits (e.g., 0010) that cause a charge to be sampled and held by a charge control capacitor (e.g., 418 in FIG. 4A). In other words, a stimulation event can cause a transition in a waveform from one level to another, and/or could cause the sampling and/or charging of charges stored on capacitors that are used to change the waveform level to another level.

Conversely, when the lead select bits and the electrode configuration bits are being used to deliver an actual stimulation pulse to patient tissue, it is possible that the charge control bits are not causing any charging and/or sampling. For a more specific example, it is possible that an entry in the stimulation event data table 522 includes 4 lead select bits (e.g., bits 0001) that cause a first one of the leads (L1) to be selected, 8 electrode select bits (e.g., bits 10000011) that cause the most distal electrode of the lead to be connected as an anode and the most proximal electrode of the lead connected as a cathode (and the other two middle electrodes to be neutral), and 4 charge control bits (e.g., 0000) that cause no charging and/or sampling.

As mentioned above, in accordance with an embodiment, each stimulation event can be defined by lead select bits (e.g., 4 bits), electrode configuration bits (e.g., 8 bits) and charge control bits (e.g., 4 bits). For example, as was explained above with reference to FIG. 1, a spinal cord stimulation system can include four implanted leads, with each lead including four electrodes. The lead select bits are used to specify which one of the four leads is being used to deliver stimulation. In specific embodiments, only one lead can deliver stimulation at one time. In an embodiment, bits 0001 can select a first lead (L1), bits 0010 can select a second lead (L2), bits 0100 can select a third lead (L3), and bit 1000 can select a fourth lead (L4). In an alternative implementation, bits 0001 can select a first lead (L1), bits 0010 can select a second lead (L2), bits 0011 can select a third lead (L3), and bits 0100 can select a forth lead (L4). In the exemplary embodiments described herein, it is assumed that the first 4 bits (i.e., the 4 most significant bits (MSBs)) of 2 bytes worth of stimulation event data are used to select a lead, but that need not be the case (i.e., more or less bits can be used to select a lead, and such bits need not be the MSBs of a block of stimulation event data). In another embodiment, three lead select bits can be used to specify which one of the four leads is being used to deliver stimulation. For example, bits 00 can select a first lead (L1), bits 01 can select a second lead (L2), bits 10 can select a third lead (L3), and bit 11 can select a fourth lead (L4), and a third bit can act as a lead enable bit. If the desire is to make sure no more than one lead can be enable at the same time, this latter embodiment advantageously makes it impossible (through an error) to enable more than one lead at a time. Other variations are also possible, and within the scope of the present invention.

The electrode configuration bits (e.g., 8 bits) can be used to specify which electrode(s) are connected as an anode (having a positive polarity), a cathode (having a negative polarity), or a neutral electrode (in which case the electrode is not used for delivering stimulation energy, i.e., is inactive). Assuming there are four electrodes on each lead, then a pair of bits (i.e., two bits) can be used to specify each electrode's configuration, in accordance with an embodiment. For example, the 2 least significant bits (LSBs) of the eight electrode configuration bits can be used to specify the configuration of a most distal electrode, the next 2 LSBs can be used to specify the configuration of the next most distal electrode, the following 2 LSBs can be used to specify the configuration of the next most distal electrode, and the 2 most significant bits (MSBs) can be used to specify the configuration of the most proximal electrode. The terms proximal and distal, as used herein, are with reference to the INS 112 to which the leads are connected. In an embodiment, one of each pair of electrode configuration bits can be used to specify whether an electrode is active or neutral, and the other one of the pair of bits can be used to specify whether an active electrode is to be connected as an anode or a cathode. For example, a 1 in the proper bit position can specify that an electrode is active, and a 0 can specify that the electrode is neutral (or vice versa); and a 1 in the proper bit position can specify that an active electrode is an anode, and a 0 can specific that an active electrode is a cathode (or vice versa). In an alternative embodiment, one of each pair of electrode configuration bits can be used to specify whether an electrode is connected as an anode, and the other one of the pair of bits can be used to specify whether the electrode is connected as a cathode. For example, bits 10 can specify that the electrode is connected as an anode, bits 01 can specify that the electrode is connected as a cathode, and bits 00 can specify that the electrode is neutral. These are just a few examples of how electrode configuration bits can be used to define the electrode configurations for a lead, which are not meant to be limiting. Other variations are also possible, and within the scope of the present invention.

In accordance with an embodiment, the charge control bits are used to control the charging and sampling of control capacitors (e.g., 418 in FIG. 4A) that store charges used to maintain, adjust and/or otherwise control charges stored by therapy output capacitors, where the therapy output capacitors are used to deliver stimulation to patient tissue. The charges stored by the control capacitors (e.g., 418 in FIG. 4A) can be generated using a plurality of digital-to-analog converters (DACs) (e.g., 414 in FIG. 4A). In an embodiment, the charge control bits (e.g., 4 bits) include one bit (e.g., a DAC chip select (CS) bit) that is used to selectively enable a chip that includes a plurality of DACs, one bit (e.g., a DAC EN bit) that is used to enable the DACs, one bit (e.g., a sample bit) that controls switches used to sample-and-hold (S/H) the outputs of the DACs, and one bit (e.g., a charge bit) that is used to appropriately charge therapy output capacitors (e.g., 430 in FIG. 4A). Other variations are also possible, and within the scope of the present invention.

As mentioned above, when triggered, the DMA channel 532 transfers stimulation event data to registers associated with the stimulation control ports 350, and the DMA channel 534 transfers next stimulation event time data to the timer compare register 544. As just explained, the stimulation event data is used to select a lead, configure the electrodes on the selected lead, and maintain stimulation output amplitudes.

In FIG. 5, two DMA channels 532 and 534 are shown as being used to copy data from portions of memory 522 and 524 (e.g., LUTs) to I/O ports, registers, or the like. It is also within the scope of the present invention that one or more additional DMA channels and one or more additional portions of memory (e.g., LUTs) can be used to control other functions. For a specific example, a third DMA channel can be used to copy stored waveform amplitude values from a portion of memory to inputs of (or registers associated with) DACs. Such a third DMA channel can, e.g., be triggered by one of the charge control bits within each block of event data. Other variations are also possible while being within the scope of the present invention.

In the above described embodiments, it was assumed that multi-bit registers, I/O ports, and the like (to which data is being transferred by the DMA channels) include parallel inputs that accept parallel transfers of data bits. However, there may be instances where a component (to which a DMA channel is to transfer data) has a serial data input (as opposed to a parallel data input). Such a component can, for example, have a serial clock input (SCLK) and a serial data input (SDI). When using a DMA channel to provide data to such a component, each block of data stored in a table can include: a serial clock bit that indicates a serial clock transition that is provided by the DMA channel to the serial clock input (e.g., a 1 bit can represent a low-to-high transition, and a 0 bit can represent a high-to-low transition, or vice versa); and a data bit that indicates the data to be serially transferred into the serial data input on a low-to-high (or high-to-low) transition of the serial clock input. For example, assuming that the component is a 16-bit DAC including a serial clock input and a serial data input, the table can include 32 separate two-bit blocks of data for each 16 bit word to be serially transferred to the DAC.

Exemplary Stimulation Signal Waveform

Figure 6:
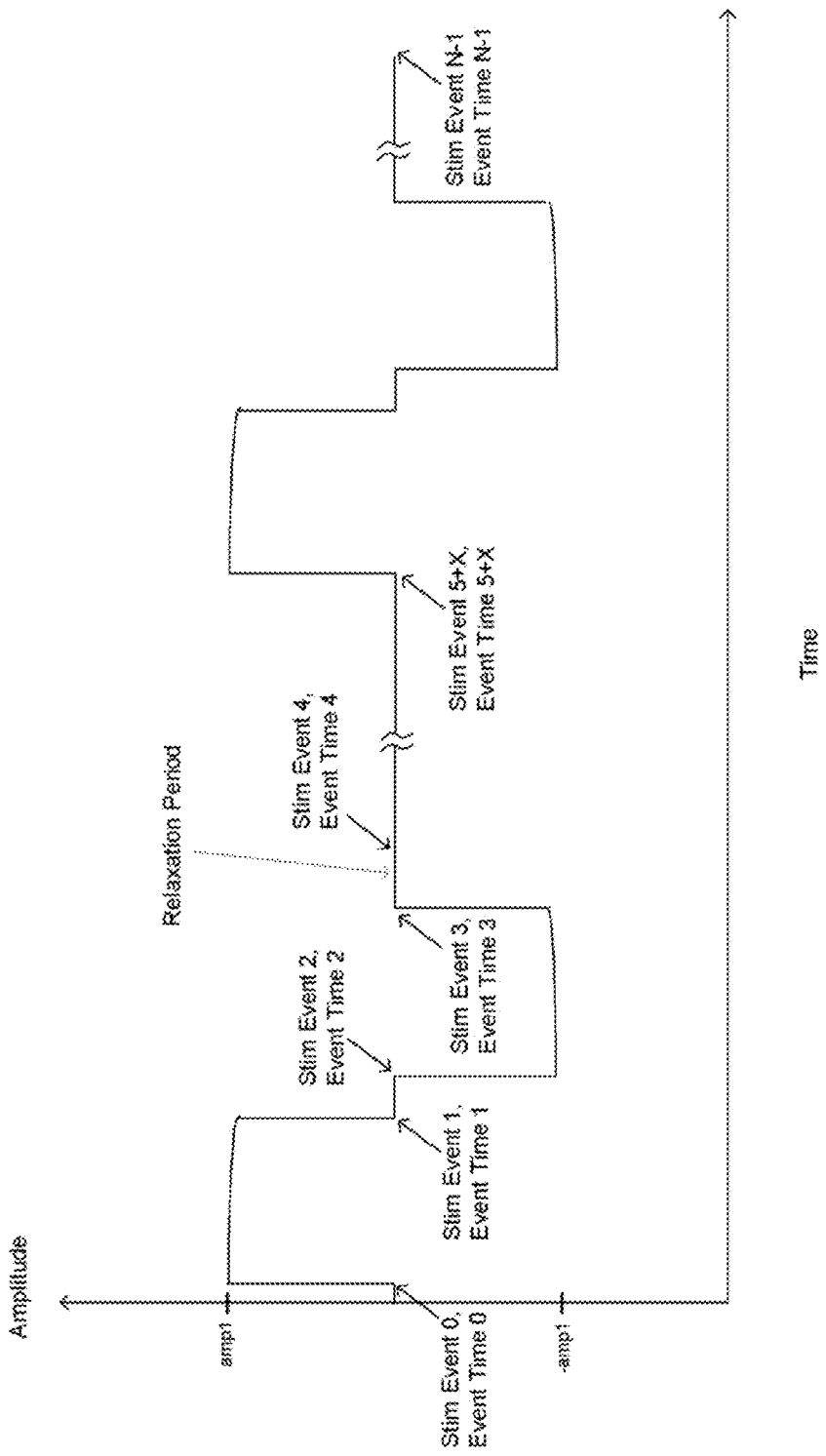
FIG. 6 illustrates an exemplary neurostimulation signal that can be generated using embodiments of the present invention.

An exemplary stimulation signal waveform is shown in FIG. 6 which is presumed to be for delivery via a first lead (lead 1 or L1) of four leads. Referring to FIG. 6, the exemplary stimulation signal waveform is shown as having a positive amplitude (amp1) starting at Event Time 0. In accordance with an embodiment, a block of stimulation event data and a block of next stimulation event time data stored in portions of memory 522 and 524, respectively, can be used to define this transition of the waveform. For example, referring back to FIGS. 4 and 5, the Event Time 0 data can specify when this event occurs, and the Stim Event 0 data can specify what occurs at this time. More specifically, the Stim Event 0 data can include: lead select bits that select lead L1 (e.g., by closing switches L1 in FIG. 5); electrode configuration bits that configure one or more electrodes of lead L1 as an anode (e.g., by closing one or more of switches SEL1-SEL4 in FIG. 5) and configure one or more electrodes of lead L1 as a cathode (e.g., by closing one or more of switches SEL5-SEL8 in FIG. 5).

Still referring to FIG. 6, between Event Time 0 and Event Time 1, the exemplary waveform is shown as generally remaining at the positive amplitude (amp 1) except for some decay due to capacitor discharge between Event Time 0 and Event Time 1. At Event Time 1, Stim Event 1 data causes the waveform to transition from the positive amplitude to zero. More specifically, the electrode configuration bits of the Stim Event 1 data can specify that all of the electrodes of lead L1 are inactive (i.e., not connected as an anode or cathode).

Still referring to FIG. 6, at Event Time 2, the exemplary waveform is shown as transitioning to a negative amplitude (−amp1). More specifically, the lead select bits of the Stim Event 2 data can specify that lead L1 is selected, and can specify that the electrode(s) configured as an anode (by Stim Event 0) are now configured as a cathode, and the electrode(s) configured as a cathode (by Stim Event 0) are now configured as an anode. In other words, the negative amplitude (−amp1) is achieved by inverting the anode/cathode configuration that was used to achieve the positive amplitude (amp1).

Between Event Time 2 and Event Time 3, the exemplary waveform is shown as generally remaining at the negative amplitude (−amp1) except for some decay due to capacitor discharge between Event Time 2 and Event Time 3. At Event Time 3, Stim Event 1 data causes the waveform to transition from the negative amplitude to zero. More specifically, electrode configuration bits of the Stim Event 3 data can specify that all of the electrodes of lead L1 are inactive (i.e., disconnected).

The exemplary waveform then returns to zero at Event Time 3, and remains at zero until at least Event Time 4. The Stim Event 3 data can specify that lead L1 is selected at Event Time 3, which can be referred to as the beginning of the "relaxation period". During this relaxation period, the electrode configuration bits (defined by Stim Event 3 data) should specify that the electrodes of lead L1 used to deliver the biphasic stimulation pulse are connected to ground to discharge any charge residual on those electrodes. Additionally, during the relaxation period from Event Time 3 to Event Time 4, the therapy output capacitor for lead L1 can be recharged. To perform this recharge, the lead select bits of Stim Event 3 should select lead L1, and the charge bit of the charge control bits should be active.

Still referring to FIG. 6, Event Time 4 represents the end of the relaxation time. As shown in FIG. 6, the next biphasic stimulation pulse to be delivered via lead L1 does not begin until Event Time 4+X. Between Event Time 4 and Event Time 4+X, stimulation pulse(s) can be delivered via one or more other lead (e.g., L2, L3 and/or L4), in accordance with stimulation event data and next stimulation event time data stored in portions of memory 522 and 524. Additionally, and/or alternatively, between Event Time 4 and Event Time 4+X, stimulation event data and next stimulation event time data can cause the charge on the charge control capacitor(s) 418 corresponding to other leads to be sampled, and/or the therapy output capacitor(s) 430 corresponding to other leads can be charged.

Clock Power Saving Features

As described above with reference to FIG. 3, the clock system 360 can generate clock signals having different frequencies that can be provided to the components of the MCU 210 and other components of the electronic circuitry 118. For example, the clock system 360 can include the main clock circuitry 362 that generates a relatively high frequency (e.g., 100 kHz) clock signal, and the auxiliary clock circuitry 364 that generates a lower frequency (e.g., 32.768 kHz) clock signal and that consumes less power than the main clock circuitry. The higher frequency clock signal generated by the main clock circuitry 362 can be used, e.g., by the CPU 310 while the CPU is performing tasks that are to be performed as fast as possible.

As explained above, in an embodiment the CPU 310 accesses neurostimulation data stored in the memory 320, and based on which "stimulation set" is activated/selected at the time, the CPU 310 generates and stores stimulation event data, and next stimulation event time data, which can be stored as two look up tables (LUTs), e.g., LUTs 522 and 524 in FIG. 5. The neurostimulation data stored in the memory 320, which is likely received from an external programmer, can include both electrode configuration information and stimulation waveform information, as explained above. The stimulation waveform information can specify, e.g., an amplitude, a pulse width and a pulse repetition rate of the stimulation waveform to be delivered.

As was described above with reference to FIG. 5, the timer counter register 542, which is incremented by a clock (CLK) signal, is compared to an event timer compare register 544 to determine when at least one of the DMA channels is/are triggered. It is this frequency of this clock signal that specifies minimum pulse width increments of a neurostimulation signal that can be achieved, wherein smaller pulse width increments allowing for higher pulse width resolution.

In an embodiment, when generating the stimulation event data and the next stimulation event time data, the CPU 310 can generate such data assuming that a specific clock signal frequency (e.g., 100 kHz) is going to be used to increment the timer counter register 542 of FIG. 5. For example, a 100 kHz clock signal provides for 10 usec pulse width increments (i.e., 1 sec/100 k=10.0 usec), while a 32.768 kHz clock provides for only 30.5 usec pulse width increments (i.e., 1 sec/32.768 k=30.5 usec). More generally, the higher the frequency of a clock signal, the smaller the pulse width increments and the greater the pulse width resolution. However, assuming similar clock circuitry is used to generate to different clock signal frequencies, the higher the frequency of a clock signal the higher the power consumption. Thus, in an embodiment power can be conserved by using the slowest clock signal that can achieve a specified pulse width resolution.

In a specific embodiment, when generating the stimulation event data and the next stimulation event time data, the CPU 310 can first determine the minimum pulse width increment necessary to achieve the neurostimulation defined by the stored neurostimulation data. Based on this determination, the CPU 310 can determine whether a clock signal generated by the lower power consuming auxiliary clock circuit 364 has sufficient resolution to be used as the clock signal that increments the timer counter register 542 of FIG. 5, or whether the clock signal generated by the higher power consuming main clock circuitry 362 needs to be used as the clock signal that increments the timer counter register 542.

If the clock signal generated by the auxiliary clock circuitry 364 has sufficient resolution to be used, then the CPU 310 generates the stimulation event data and the next stimulation event time data assuming that the lower clock signal frequency generated by the auxiliary clock circuitry 364 will be used to increment the timer counter register 542. This also enables the main clock circuitry 362 (so long as its not needed for other purposes) to be at least partially disabled during periods of time when the DMA controller 330 is controlling neurostimulation. If on the other hand the clock signal generated by the auxiliary clock circuitry 364 does not have sufficient resolution to be used (i.e., clock signal generated the main clock circuitry is need), then the CPU 310 generates the stimulation event data and the next stimulation event time data assuming that the higher clock signal frequency generated by the main clock circuitry 362 will be used to increment the timer counter register 542. In this latter case, the auxiliary clock circuit 364 can be at least partially disabled when it is not being used, to conserve power.

In still other embodiments, the frequency of a clock signal generated by the auxiliary clock circuit 364 is adjustable, and an optimal or near optimal frequency can be selected for controlling delivery of the stimulation waveforms associated with a selected stimulation set. For example, the frequency of the auxiliary clock circuit 364 can be programmed to be the slowest clock signal frequency that provides the signal resolution desired and the other events necessary to produce the desired signal. The CPU 310 can determine this frequency, and generate the stimulation event data and the next stimulation event time data based on the determined frequency.

In the exemplary embodiments described above with reference to FIG. 1-6, a first DMA channel was described as being used to transfer stimulation event data (stored in a first portion of memory) to I/O ports or registers to thereby change the state of circuitry, and a second DMA channel was used to transfer next stimulation event timing data (stored in a second portion of memory) a timer that is used to control timing associated with the stimulation events. In other embodiments, more than two DMA channels can be utilized. For example, a third DMA channel can be used for transferring amplitude values (stored in a third portion of memory) that are used to control the amplitudes of stimulation waveforms.

As mentioned above, embodiments of the present invention can be used to control neurostimulation for patients with chronic pain. For example, conditions that may be treated using embodiments of the present invention include, but are not limited to: Failed Back Surgery syndrome; Chronic Intractable Low Back Pain due to Lumbar facet disease as evidenced by diagnostic block(s), Sacroiliac Joint disease as evidenced by diagnostic block(s), Spinal Stenosis, Nerve root impingement—non-surgical candidates, Discogenic Pain— discography based or not, or due to an unknown etiology; Complex Regional Pain Syndrome; Post-Herpetic Neuralgia; Diabetic Neuropathic Pain; Intractable Painful Peripheral Vascular Disease; Raynaud's Phenomenon; Phantom Limb Pain; Generalized Deaffrentation Pain Conditions; Chronic, Intractable Angina; Cervicogenic Headache; Various Visceral Pains (e.g., pancreatitis, etc.); Post-Mastectomy Pain; Vuvlodynia; Orchodynia; Painful Autoimmune Disorders; Post-Stroke Pain with limited painful distribution; Repeated, localized sickle cell crisis; Lumbar Radiculopathy; Thoracic Radiculopathy; Cervical Radiculopathy; Cervical axial neck pain, "whiplash"; and Multiple Sclerosis with limited pain distribution.

Embodiments of the present invention can also be used for treating non-painful indications or conditions, such as, but not limited to: Parkinson's Disease, Multiple Sclerosis, Demylenating Movement Disorders, Physical and Occupational Therapy Assisted Neurostimulation, Spinal Cord Injury—Neuroregeneration Assisted Therapy, Asthma, Chronic Heart Failure, Obesity, Stroke—such as Acute Ischemia.

Neurostimulation, as mentioned above, can be delivered to or adjacent a patient's spinal cord or a portion thereof, including, but not limited to, stimulation of a dorsal root or dorsal root ganglion. Neurostimulation can alternatively be brain type neurostimulation, such as, but not limited to, cranial, transcranial, cortical, subcortical, cerebellar or deep brain.

Embodiments of the present invention may also be used to control types of stimulation other than neurostimulation, such as, but not limited to, cardiac stimulation. For example, stimulation event data and next stimulation event timing data can be transferred by DMA channels to appropriate circuitry to control cardiac pacing type stimulation that is performed whenever an R-wave (or other type of wave or complex) is not detected within a window of time following a previous R-wave or paced event (or other cardiac event). This is just an example, which is not meant to be limiting.

Embodiments of the present invention can also be used for controlling implantable drug pumps and other implantable, non-implantable, or partially implantable medical devices.

Embodiments of the present invention have been described above with the aid of functional building blocks illustrating the performance of specified functions and relationships thereof. The boundaries of these functional building blocks have sometimes been defined herein for the convenience of the description. Alternate boundaries can be defined so long as the specified functions and relationships thereof are appropriately performed. Any such alternate boundaries are thus within the scope and spirit of the claimed invention.

Although the foregoing invention has been described in some detail by way of illustration and example, for purposes of clarity and understanding, it will be obvious that various alternatives, modifications and equivalents may be used and the above description should not be taken as limiting in scope of the invention.

What is claimed is:

1. An implantable stimulation system, comprising:
memory including
   a first table that stores blocks of stimulation event data corresponding to stimulation events that are to be performed during a period of time; and
   a second table that stores blocks of next stimulation event time data corresponding to the period of time; and
a direct memory access (DMA) controller including
   a first DMA channel that selectively transfers one of the blocks of stimulation event data from the first table to one or more registers that are used to control stimulation events; and
   a second DMA channel that selectively transfers one of the blocks of next stimulation event time data from the second table to a timer that is used to control timing associated with the stimulation events.

2. The implantable stimulation system of claim 1, further comprising:
   a timer including a count register and a first compare register;
   wherein each of the blocks of next stimulation event time data comprises a value, which when transferred by the second DMA channel to the timer is stored in the first compare register of the timer;
   wherein the count register of the timer stores a count value and increments the count value in dependence on a clock signal;
   wherein the first compare register compares the value stored in the first compare register to the count value of the count register, and generates a first trigger when the value stored in the first compare register equals the count value of the count register; and
   wherein the first DMA channel transfers a next block of the stimulation event data from the first table to the one or more registers that are used to control stimulation events in dependence on the first trigger generated by the first compare register.

3. The implantable stimulation system of claim 2, wherein the second DMA channel transfers a next block of the next stimulation event time data from the second table to the first compare register in dependence on one of the following:
   the first trigger generated by the first compare register;
   a trigger signal generated in response to the first DMA channel starting a transfer; or
   a trigger signal generated in response to the first DMA channel completing a transfer.

4. The implantable stimulation system of claim 3, wherein:
   the timer also includes a second compare register that stores a reset value and compares the reset value to the count value of the count register; and
   when the stored reset value equals the count value of the count register, the count value of the count register is reset.

5. The implantable stimulation system of claim 1, wherein the one or more registers that are used to control the stimulation events correspond to I/O ports of a microcontroller unit (MCU) that includes the DMA controller and the memory.

6. The implantable stimulation system of claim 5, wherein each of the blocks of stimulation event data corresponds to a stimulation event and includes:
   a first group of bits that specify which one of a plurality of leads, if any, is selected for the stimulation event; and
   a second group of bits that specify how electrodes of a selected lead are connected during the stimulation event;
   wherein the first group of bits are transferred by the first DMA channel to a first portion of the one or more registers that correspond to I/O ports connected to circuitry that controls lead selection; and
   wherein the second group of bits are transferred by the first DMA channel to a second portion of the one or more registers that correspond to I/O ports connected to circuitry that controls electrode configuration.

7. The implantable stimulation system of claim 1, further comprising:
   a central processing unit (CPU) that receives or otherwise accesses stimulation data that defines stimulation signals to be delivered via one or more leads;
   wherein based on the stimulation data, the CPU generates the first and second tables that are stored in the memory; and
   wherein after the CPU generates the first and second tables, the DMA controller controls the stimulation events for the period of time without CPU intervention, thereby enabling the CPU to perform other tasks unrelated to performing the stimulation events and/or to enter a low-power mode during the period of time.

8. An implantable stimulation system, comprising:
   a central processing unit (CPU) that receives or otherwise accesses stimulation data that defines stimulation signals to be delivered via one or more leads;
   memory including
      a first table that stores blocks of stimulation event data corresponding to stimulation events that are to be performed during a period of time and
      a second table that stores blocks of next stimulation event time data corresponding to the period of time
   a timer including a count register that is used to control timing associated with the stimulation events;
   a direct memory access (DMA) controller including
      a first DMA channel that selectively transfers one of the blocks of stimulation event data from the first table to one or more registers that are used to control the stimulation events; and
      a second DMA channel that selectively transfers one of the blocks of next stimulation event time data from the second table to the timer that is used to control timing associated with the stimulation events;
   wherein the CPU identifies potential pulse collisions based on the stimulation data; and
   wherein the CPU generates the first and second tables so that the identified potential pulse collisions are avoided when the DMA controller controls the stimulation events for the period of time in dependence on the first and second tables; and
   wherein after the CPU generates the first and second tables, the DMA controller controls the stimulation events for the period of time without CPU intervention, thereby enabling the CPU to perform other tasks unrelated to performing the stimulation events and/or to enter a low-power mode during the period of time.

9. An implantable stimulation system, comprising:
   a central processing unit (CPU) that receives or otherwise accesses stimulation data that defines stimulation signals to be delivered via one or more leads;

memory including
- a first table that stores blocks of stimulation event data corresponding to stimulation events that are to be performed during a period of time; and
- a second table that stores blocks of next stimulation event time data corresponding to the period of time a timer including a count register that is used to control timing associated with the stimulation events;

a direct memory access (DMA) controller including
- a first DMA channel that selectively transfers one of the blocks of stimulation event data from the first table to one or more registers that are used to control the stimulation events; and
- a second DMA channel that selectively transfers one of the blocks of next stimulation event time data from the second table to the timer that is used to control timing associated with the stimulation events;

a first clock circuit that generates the first clock signal that is used by the count register to increment the count value; and a second clock circuit that generates a second clock signal that is used by the CPU when the CPU is not in a low-power mode;

wherein based on the stimulation data, the CPU generates the first and second tables that are stored in the memory;

wherein after the CPU generates the first and second tables, the DMA controller controls the stimulation events for the period of time without CPU intervention, thereby enabling the CPU to perform other tasks unrelated to performing the stimulation events and/or to enter the low-power mode during the period of time;

wherein the second clock signal generated by the second clock circuit has a higher frequency than the first clock signal generated by the first clock circuit, which causes the second clock circuit to consume more power than the first clock circuit; and wherein the second clock circuit is at least partially disabled when the CPU is in the low-power mode.

10. An implantable stimulation system, comprising:

a central processing unit (CPU) that receives or otherwise accesses stimulation data that defines stimulation signals to be delivered via one or more leads;

memory including
- a first table that stores blocks of stimulation event data corresponding to stimulation events that are to be performed during a period of time; and
- a second table that stores blocks of next stimulation event time data corresponding to the period of time;

a timer including a count register that is used to control timing associated with the stimulation events;

a direct memory access (DMA) controller including
- a first DMA channel that selectively transfers one of the blocks of stimulation event data from the first table to one or more registers that are used to control the stimulation events; and
- a second DMA channel that selectively transfers one of the blocks of next stimulation event time data from the second table to the timer that is used to control timing associated with the stimulation events;

a first clock circuit that generates a clock signal having a first frequency; and a second clock circuit that generates a clock signal having a second frequency that is higher than the first frequency and that is used by the CPU when the CPU is not in a low-power mode;

wherein the second clock circuit consumes more power than the first clock circuit;

wherein based on the stimulation data received or otherwise accessed by the CPU, the CPU determines whether the clock signal generated by the first clock circuit has sufficient resolution to be used as the first clock signal that the count register uses to increment the count value, or whether the clock signal generated by the second clock circuit needs to be used as the first clock signal that the count register uses to increment the count value;

wherein if the clock signal generated by the first clock circuit has sufficient resolution to be used as the first clock signal that the count register uses to increment the count value, then the clock signal generated by the first clock circuit is used as the first clock signal and the second clock circuit is at least partially disabled; and wherein if the clock signal generated by the second clock circuit needs to be used as the first clock signal that the count register uses to increment the count value, then the clock signal generated by the second clock circuit is used as the first clock signal and the first clock circuit is at least partially disabled.

11. The implantable stimulation system of claim 10, wherein:
the first and second tables are generated by the CPU in dependence on whether the clock signal having the first frequency or the clock signal having the second frequency is used as the first clock signal.

12. A method for use with an implantable stimulation system, the method comprising:
storing, in a first table, blocks of stimulation event data corresponding to stimulation events that are to be performed during a period of time; and
storing, in a second table, blocks of next stimulation event time data corresponding to the period of time; and
using a first direct memory access (DMA) channel of a DMA controller to selectively transfer one of the blocks of stimulation event data from the first table to one or more registers that are used to control stimulation events; and
using a second DMA channel of the DMA controller to selectively transfer one of the blocks of next stimulation event time data from the second table to a timer that is used to control timing associated with the stimulation events.

13. The method of claim 12, wherein each of the blocks of next stimulation event time data comprises a value, which when transferred by the second DMA channel to the timer is stored in a first compare register of the timer, and further comprising:
incrementing a count value in dependence on a clock signal;
comparing the value stored in the first compare register to the count value;
generating a first trigger when the value stored in the first compare register equals the count value of the count register; and
using the first DMA channel to transfer a next block of the stimulation event data from the first table to the one or more registers that are used to control stimulation events in dependence on the first trigger.

14. The method of claim 12, wherein the one or more registers that are used to control the stimulation events correspond to I/O ports of a microcontroller unit (MCU) that includes the DMA controller.

15. The method of claim 14, wherein each of the blocks of stimulation event data corresponds to a stimulation event and includes:

a first group of bits that specify which one of a plurality of leads, if any, is selected for the stimulation event; and a second group of bits that specify how the electrodes of a selected lead are connected during the stimulation event;

wherein the first group of bits are transferred by the first DMA channel to a first portion of the one or more registers that correspond to I/O ports connected to circuitry that controls lead selection; and wherein the second group of bits are transferred by the first DMA channel to a second portion of the one or more registers that correspond to I/O ports connected to circuitry that controls electrode configuration.

16. The method of claim 12, further comprising:

using a CPU to generate the first and second tables based on stimulation data that defines stimulation signals to be delivered via one or more leads; and after using the CPU to generate the first and second tables, using the DMA controller to control the stimulation events for the period of time without CPU intervention, thereby enabling the CPU to perform other tasks unrelated to performing the stimulation events and/or to enter a low-power mode during the period of time.

17. The method of claim 16, further comprising identifying potential pulse collisions based on the stimulation data; and when using the CPU to generate the first and second tables, generating the first and second tables so that the identified potential pulse collisions are avoided when the DMA controller controls the stimulation events for the period of time in dependence on the first and second tables.

18. The method of claim 16, further comprising:

using a first clock circuit to generate a clock signal having a first frequency; and using a second clock circuit to generate a clock signal having a second frequency that is higher than the first frequency and that is used by the CPU when the CPU is not in the low-power mode, wherein the second clock circuit consumes more power than the first clock circuit;

based on the stimulation data, determining whether the clock signal generated by the first clock circuit has sufficient resolution to be used as the first clock signal that is used to increment a count value that is used to control timing associated with the stimulation events, or whether the clock signal generated by the second clock circuit needs to be used as the first clock signal that is used to increment the count value;

wherein if the clock signal generated by the first clock circuit has sufficient resolution to be used as the first clock signal that is used to increment the count value, then using the clock signal generated by the first clock circuit as the first clock signal and at least partially disabling the second clock circuit; and wherein if the clock signal generated by the second clock circuit needs to be used as the first clock signal that is used to increment the count value, then using the clock signal generated by the second clock circuit as the first clock signal and at least partially disabling the first clock circuit.

19. The method of claim 18, wherein:

the first and second tables are generated by the CPU in dependence on whether the clock signal having the first frequency or the clock signal having the second frequency is used as the first clock signal.

20. An implantable stimulation system comprising:

a plurality of leads, wherein each lead includes a plurality of electrodes, and wherein each electrode is connectable as an anode, as a cathode, or as a neutral electrode;

a central processing unit (CPU);

a plurality of ports;

memory that stores a block of stimulation event data for each of a plurality of stimulation events that are to occur during a predetermined period of time, wherein each block of stimulation event data specifies, which said lead, if any, is selected for the stimulation event, and how said electrodes of said selected lead, if any, are connected during the stimulation event, and a block of next stimulation event time data for each of the plurality of stimulation events that are to occur during the predetermined period of time, wherein each block of next stimulation event time data specifies when a next one of the plurality of stimulation events starts;

a timer including a count register that stores a count value and increments the count value in dependence on a first clock signal, and a first compare register that stores a time value corresponding to one of the blocks of the next stimulation event time data, compares the time value to the count value of the count register, and generates a first trigger when the time value equals the count value of the count register; and a direct memory access (DMA) controller including a first DMA channel that transfers one block of stimulation event data at a time, from the memory to the ports without CPU intervention, in dependence on the first trigger generated by the first compare register, and a second DMA channel that transfers one block of next stimulation event time data at a time, from the memory to the first compare register without CPU intervention, in dependence on the first trigger generated by the first compare register or in dependence on the first DMA channel starting or completing a transfer.

21. The implantable stimulation system of claim 20, wherein:

the timer also includes a second compare register that stores a second value, compares the second value to the count value of the count register, and generates a second trigger when the stored second value equals the count value of the count register;

the second value specifies the predetermined period of time; and the second trigger causes the count value stored by the count register to be reset.

22. The implantable stimulation system of claim 21, wherein the memory comprises:

a first table that stores the stimulation event data for each of a plurality of stimulation events that are to occur during the predetermined period of time; and a second table that stores the next stimulation event time data for each of the plurality of stimulation events that are to occur during the predetermined period of time.

23. The implantable stimulation system of claim 21, wherein the first and second DMA channels are re-initialized in response to at least one of the following events:

(i) the first DMA channel transfers the last stimulation event data stored in the first table to the ports;

(ii) the second DMA channel transfers the last next stimulation event time data stored in the second table to the first compare register; or (iii) the second trigger causes the count value stored by the count register to be reset.

24. The implantable stimulation system of claim 20, wherein the CPU, the ports, the memory, the timer, and the DMA controller are components of a same microcontroller unit (MCU).

25. The implantable stimulation system of claim 20, wherein:

the CPU receives or otherwise accesses stimulation data that defines stimulation signals to be delivered via the leads;

the CPU identifies potential pulse collisions based on the stimulation data; and the CPU generates the first and second tables so that the identified potential pulse collisions are avoided when the DMA controller controls the stimulation events for the period of time in dependence on the first and second tables; and after the CPU generates the first and second tables, the DMA controller controls the stimulation events for the period of time without CPU intervention, thereby enabling the CPU to perform other tasks unrelated to performing the stimulation events and/or to enter a low-power mode during the period of time.

26. The implantable stimulation system of claim 20, further comprising:

a first clock circuit that generates the first clock signal that is used by the count register to increment the count value; and a second clock circuit that generates a second clock signal that is used by the CPU when the CPU is not in the low-power mode;

wherein the CPU receives or otherwise accesses stimulation data that defines stimulation signals to be delivered via the leads;

wherein based on the stimulation data, the CPU generates the first and second tables that are stored in the memory;

wherein after the CPU generates the first and second tables, the DMA controller controls the stimulation events for the period of time without CPU intervention, thereby enabling the CPU to perform other tasks unrelated to performing the stimulation events and/or to enter a low-power mode during the period of time;

wherein the second clock signal generated by the second clock circuit has a higher frequency than the first clock signal generated by the first clock circuit, which causes the second clock circuit to consume more power than the first clock circuit; and wherein the second clock circuit is at least partially disabled when the CPU is in the low-power mode.

27. The implantable stimulation system of claim 20, further comprising:

a first clock circuit that generates a clock signal having a first frequency; and a second clock circuit that generates a clock signal having a second frequency that is higher than the first frequency and that is used by the CPU when the CPU is not in the low-power mode;

wherein the second clock circuit consumes more power than the first clock circuit;

wherein the CPU receives or otherwise accesses stimulation data that defines stimulation signals to be delivered via the leads;

wherein based on the stimulation data received or otherwise accessed by the CPU, the CPU determines whether the clock signal generated by the first clock circuit has sufficient resolution to be used as the first clock signal that the count register uses to increment the count value, or whether the clock signal generated by the second clock circuit needs to be used as the first clock signal that the count register uses to increment the count value;

wherein if the clock signal generated by the first clock circuit has sufficient resolution to be used as the first clock signal that the count register uses to increment the count value, then the clock signal generated by the first clock circuit is used as the first clock signal and the second clock circuit is at least partially disabled; and wherein if the clock signal generated by the second clock circuit needs to be used as the first clock signal that the count register uses to increment the count value, then the clock signal generated by the second clock circuit is used as the first clock signal and the first clock circuit is at least partially disabled.

28. The implantable stimulation system of claim 27, wherein:

the first and second tables are generated by the CPU in dependence on whether the clock signal having the first frequency or the clock signal having the second frequency is used as the first clock signal.

* * * * *